(12) United States Patent
Scheckel

(10) Patent No.: US 10,107,299 B2
(45) Date of Patent: Oct. 23, 2018

(54) FUNCTIONAL ELEMENT, IN PARTICULAR FLUID PUMP, HAVING A HOUSING AND A CONVEYING ELEMENT

(75) Inventor: Mario Scheckel, Berlin (DE)

(73) Assignee: ECP ENTWICKLUNGSGESELLSCHAFT MBH, Berlin (DE)

( * ) Notice: Subject to any disclaimer, the term of this patent is extended or adjusted under 35 U.S.C. 154(b) by 621 days.

(21) Appl. No.: 13/261,216

(22) PCT Filed: Sep. 22, 2010

(86) PCT No.: PCT/EP2010/005865
§ 371 (c)(1),
(2), (4) Date: May 17, 2012

(87) PCT Pub. No.: WO2011/035925
PCT Pub. Date: Mar. 31, 2011

(65) Prior Publication Data
US 2012/0234411 A1 Sep. 20, 2012

Related U.S. Application Data

(60) Provisional application No. 61/244,608, filed on Sep. 22, 2009.

(30) Foreign Application Priority Data

Sep. 22, 2009 (EP) .................................... 09075439

(51) Int. Cl.
*F04D 29/18* (2006.01)
*A61M 1/10* (2006.01)
*A61M 1/12* (2006.01)

(52) U.S. Cl.
CPC ........... *F04D 29/181* (2013.01); *A61M 1/101* (2013.01); *A61M 1/1012* (2014.02);
(Continued)

(58) Field of Classification Search
CPC ...... F04D 29/002; F04D 29/181; F04D 29/18; F04B 45/04; F04B 45/02; F04B 43/0054;
(Continued)

(56) References Cited

U.S. PATENT DOCUMENTS 3,007,416 A * 11/1961 Childs ........................... 417/383
3,510,229 A 5/1970 Smith et al.
(Continued)

FOREIGN PATENT DOCUMENTS

| CA | 1008330 A1 | 4/1977 |
| CA | 2311977 A1 | 12/2000 |

(Continued)

*Primary Examiner* — Peter J Bertheaud
*Assistant Examiner* — Dnyanesh Kasture
(74) *Attorney, Agent, or Firm* — White & Case LLP

(57) ABSTRACT

The invention relates to a fluid pump having a housing delimiting a fluid chamber and having a conveying element for the fluid disposed in the fluid chamber, the housing, with respect to the shape and/or size thereof, being able to be changed between at least a first, expanded state and a second, compressed state. The object, to stabilize adequately a corresponding housing, is achieved according to the invention by the housing having at least one stabilization chamber which can be supplied with a fluid pressure and is different from the fluid chamber, the first state of the housing being assigned to a first fluid pressure in the stabilization chamber and the second state of the housing being assigned to a second fluid pressure.

27 Claims, 5 Drawing Sheets

(52) U.S. Cl.
CPC ......... *A61M 1/1024* (2014.02); *A61M 1/1034* (2014.02); *A61M 1/1098* (2014.02); *A61M 1/122* (2014.02); *A61M 1/125* (2014.02); *A61M 2205/0266* (2013.01); *Y10T 137/85978* (2015.04)

(58) Field of Classification Search
CPC .... F04B 43/0072; F04B 43/08; F04B 43/107; F04B 43/113; F04B 45/033; F04B 45/0333; F04B 45/0336; F04B 45/06; F04B 45/061; F04B 45/062; F04B 45/0733; F04B 11/00; F04B 39/0027; A61M 1/1024; A61M 1/1044; A61M 1/1072; A61M 1/1074; A61M 1/125; A61M 1/122; A61M 1/1098; A61M 1/1034; A61M 1/1012; A61M 2205/0266; A61M 1/101
USPC ....... 417/205, 206, 285, 389, 390, 392, 394, 417/540, 472; 600/18; 604/908, 914
See application file for complete search history.

(56) References Cited

U.S. PATENT DOCUMENTS

| | | | |
|---|---|---|---|
| 3,568,659 A | 3/1971 | Karnegis | |
| 3,662,487 A * | 5/1972 | Seefluth | 446/37 |
| 3,802,551 A | 4/1974 | Somers | |
| 3,812,812 A | 5/1974 | Hurwitz | |
| 4,014,317 A | 3/1977 | Bruno | |
| 4,207,028 A | 6/1980 | Ridder | |
| 4,559,951 A | 12/1985 | Dahl et al. | |
| 4,563,181 A | 1/1986 | Wijayarathna et al. | |
| 4,679,558 A | 7/1987 | Kensey et al. | |
| 4,686,982 A | 8/1987 | Nash | |
| 4,747,821 A | 5/1988 | Kensey et al. | |
| 4,749,376 A | 6/1988 | Kensey et al. | |
| 4,753,221 A * | 6/1988 | Kensey et al. | 600/16 |
| 4,801,243 A | 1/1989 | Norton | |
| 4,817,613 A | 4/1989 | Jaraczewski et al. | |
| 4,919,647 A | 4/1990 | Nash | |
| 4,957,504 A | 9/1990 | Chardack | |
| 4,969,865 A | 11/1990 | Hwang et al. | |
| 4,995,857 A | 2/1991 | Arnold | |
| 5,011,469 A | 4/1991 | Buckberg et al. | |
| 5,040,944 A | 8/1991 | Cook | |
| 5,042,984 A | 8/1991 | Kensey et al. | |
| 5,052,404 A | 10/1991 | Hodgson | |
| 5,061,256 A | 10/1991 | Wampler | |
| 5,092,844 A * | 3/1992 | Schwartz et al. | 604/151 |
| 5,097,849 A | 3/1992 | Kensey et al. | |
| 5,108,411 A | 4/1992 | McKenzie | |
| 5,112,292 A | 5/1992 | Hwang et al. | |
| 5,112,347 A * | 5/1992 | Taheri | 606/200 |
| 5,113,872 A | 5/1992 | Jahrmarkt et al. | |
| 5,117,838 A | 6/1992 | Palmer et al. | |
| 5,118,264 A | 6/1992 | Smith | |
| 5,145,333 A | 9/1992 | Smith | |
| 5,163,910 A | 11/1992 | Schwartz et al. | |
| 5,169,378 A * | 12/1992 | Figuera | 600/16 |
| 5,183,384 A | 2/1993 | Trumbly | |
| 5,191,888 A | 3/1993 | Palmer et al. | |
| 5,201,679 A | 4/1993 | Velte, Jr. et al. | |
| 5,275,580 A | 1/1994 | Yamazaki | |
| 5,370,685 A * | 12/1994 | Stevens | 623/2.11 |
| 5,373,619 A | 12/1994 | Fleischhacker et al. | |
| 5,376,114 A | 12/1994 | Jarvik | |
| 5,501,574 A | 3/1996 | Raible | |
| 5,531,789 A | 7/1996 | Yamazaki et al. | |
| 5,620,309 A * | 4/1997 | Todden et al. | 417/199.2 |
| 5,701,911 A | 12/1997 | Sasamine et al. | |
| 5,755,784 A | 5/1998 | Jarvik | |
| 5,776,190 A | 7/1998 | Jarvik | |
| 5,813,405 A | 9/1998 | Montano, Jr. et al. | |
| 5,820,542 A | 10/1998 | Dobak, III et al. | |
| 5,820,571 A | 10/1998 | Erades et al. | |
| 5,827,171 A | 10/1998 | Dobak, III et al. | |
| 5,851,174 A | 12/1998 | Jarvik et al. | |
| 5,882,329 A | 3/1999 | Patterson et al. | |
| 5,888,241 A | 3/1999 | Jarvik | |
| 5,911,685 A * | 6/1999 | Siess et al. | 600/16 |
| 5,928,132 A * | 7/1999 | Leschinsky | 600/16 |
| 5,938,672 A | 8/1999 | Nash | |
| 5,954,745 A * | 9/1999 | Gertler et al. | 606/200 |
| 5,971,208 A * | 10/1999 | Kennedy | 222/54 |
| 6,030,397 A | 2/2000 | Monetti et al. | |
| 6,129,704 A | 10/2000 | Forman et al. | |
| 6,152,693 A | 11/2000 | Olsen et al. | |
| 6,168,624 B1 | 1/2001 | Sudai | |
| 6,254,359 B1 | 7/2001 | Aber | |
| 6,302,910 B1 | 10/2001 | Yamazaki et al. | |
| 6,308,632 B1 | 10/2001 | Shaffer | |
| 6,336,939 B1 | 1/2002 | Yamazaki et al. | |
| 6,346,120 B1 | 2/2002 | Yamazaki et al. | |
| 6,387,125 B1 | 5/2002 | Yamazaki et al. | |
| 6,503,224 B1 | 1/2003 | Forman et al. | |
| 6,506,025 B1 | 1/2003 | Gharib | |
| 6,508,787 B2 | 1/2003 | Erbel et al. | |
| 6,517,315 B2 | 2/2003 | Belady | |
| 6,527,521 B2 | 3/2003 | Noda | |
| 6,533,716 B1 * | 3/2003 | Schmitz-Rode et al. | 600/16 |
| 6,537,030 B1 | 3/2003 | Garrison | |
| 6,537,315 B2 | 3/2003 | Yamazaki et al. | |
| 6,592,612 B1 | 7/2003 | Samson et al. | |
| 6,652,548 B2 | 11/2003 | Evans et al. | |
| 6,719,791 B1 | 4/2004 | Nusser | |
| 6,790,171 B1 * | 9/2004 | Grundeman | A61M 1/101 600/18 |
| 6,860,713 B2 | 3/2005 | Hoover | |
| 6,945,977 B2 | 9/2005 | Demarais et al. | |
| 6,981,942 B2 * | 1/2006 | Khaw et al. | 600/16 |
| 7,022,100 B1 | 4/2006 | Aboul-Hosn et al. | |
| 7,027,875 B2 | 4/2006 | Siess et al. | |
| 7,074,018 B2 | 7/2006 | Chang | |
| 7,179,273 B1 | 2/2007 | Palmer et al. | |
| 7,393,181 B2 | 7/2008 | McBride et al. | |
| 7,467,929 B2 | 12/2008 | Nusser et al. | |
| 7,731,675 B2 | 6/2010 | Aboul-Hosn et al. | |
| 7,927,068 B2 * | 4/2011 | McBride | A61M 1/101 415/131 |
| 7,934,909 B2 | 5/2011 | Neusser et al. | |
| 7,942,804 B2 | 5/2011 | Khaw | |
| 2002/0123661 A1 | 9/2002 | Verkerke et al. | |
| 2003/0135086 A1 | 7/2003 | Khaw et al. | |
| 2003/0231959 A1 | 12/2003 | Snider | |
| 2004/0034272 A1 * | 2/2004 | Diaz et al. | 600/18 |
| 2004/0044266 A1 | 3/2004 | Siess et al. | |
| 2004/0046466 A1 | 3/2004 | Siess et al. | |
| 2004/0064089 A1 * | 4/2004 | Kesten et al. | 604/93.01 |
| 2004/0093074 A1 | 5/2004 | Hildebrand et al. | |
| 2004/0215222 A1 | 10/2004 | Krivoruchko | |
| 2004/0215228 A1 | 10/2004 | Simpson et al. | |
| 2005/0233097 A1 * | 10/2005 | Tojo et al. | 428/32.26 |
| 2006/0008349 A1 | 1/2006 | Khaw | |
| 2006/0062672 A1 | 3/2006 | McBride et al. | |
| 2006/0195004 A1 | 8/2006 | Jarvik | |
| 2008/0132747 A1 | 6/2008 | Shifflette | |
| 2008/0132748 A1 * | 6/2008 | Shifflette | 600/16 |
| 2008/0262584 A1 | 10/2008 | Bottomley et al. | |
| 2008/0306327 A1 | 12/2008 | Shifflette | |
| 2009/0060743 A1 | 3/2009 | McBride et al. | |
| 2009/0093764 A1 | 4/2009 | Pfeffer et al. | |
| 2009/0093796 A1 | 4/2009 | Pfeffer et al. | |
| 2010/0041939 A1 | 2/2010 | Siess | |
| 2010/0087773 A1 | 4/2010 | Ferrari | |
| 2010/0268011 A1 | 10/2010 | Siess | |
| 2011/0238172 A1 | 9/2011 | Akdis | |
| 2011/0275884 A1 | 11/2011 | Scheckel | |
| 2012/0039711 A1 | 2/2012 | Roehn | |
| 2012/0041254 A1 | 2/2012 | Scheckel | |
| 2012/0046648 A1 | 2/2012 | Scheckel | |
| 2012/0093628 A1 | 4/2012 | Liebing | |
| 2012/0101455 A1 | 4/2012 | Liebing | |

(56) References Cited

U.S. PATENT DOCUMENTS

| | | |
|---|---|---|
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner |
| 2013/0204362 A1 | 8/2013 | Toellner |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2701809 A1 | 4/2009 |
| CA | 2701810 | 4/2009 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 41 24 299 A1 | 1/1992 |
| DE | 4124299 A1 | 1/1992 |
| DE | 69103295 T2 | 12/1994 |
| DE | 19535781 A1 | 3/1997 |
| DE | 19711935 A1 | 4/1998 |
| DE | 69407869 T2 | 4/1998 |
| DE | 29804046 U1 | 6/1998 |
| DE | 69017784 T3 | 4/2000 |
| DE | 69427390 T2 | 9/2001 |
| DE | 10059714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 10 2007 012 817 A1 | 9/2008 |
| DE | 102010011998 A1 | 9/2010 |
| EP | 0480102 A1 | 4/1992 |
| EP | 0560000 A2 | 9/1993 |
| EP | 0629412 B1 | 1/1998 |
| EP | 0884064 A2 | 12/1998 |
| EP | 0916359 A1 | 5/1999 |
| EP | 1066851 A1 | 1/2001 |
| EP | 0914171 B1 | 10/2001 |
| EP | 0768091 B1 | 7/2003 |
| EP | 0951302 B1 | 9/2004 |
| EP | 1114648 B1 | 9/2005 |
| EP | 1019117 B1 | 11/2006 |
| EP | 1337288 B1 | 3/2008 |
| EP | 2 047 872 A1 | 4/2009 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 1651290 B1 | 1/2012 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 A | 7/1991 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 94001148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 0027446 A1 | 5/2000 |
| WO | 0043054 A2 | 7/2000 |
| WO | 0062842 | 10/2000 |
| WO | 2001007760 A1 | 2/2001 |
| WO | 2001007787 A1 | 2/2001 |
| WO | 2001083016 A2 | 11/2001 |
| WO | 2003057013 A2 | 7/2003 |
| WO | 2003103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

\* cited by examiner

Fig. 4
Fig. 5
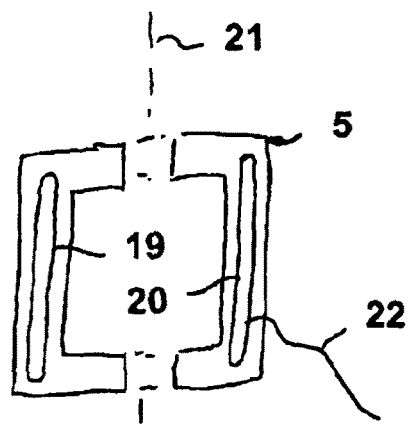
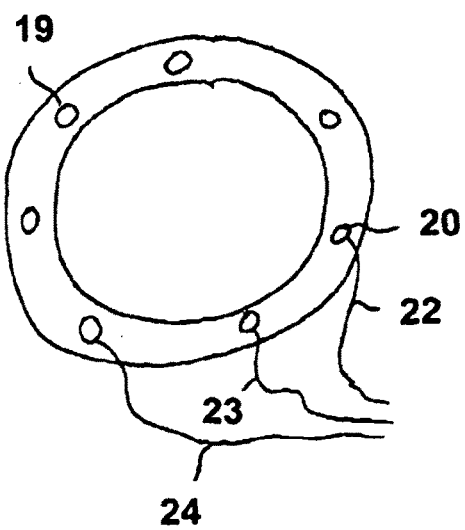
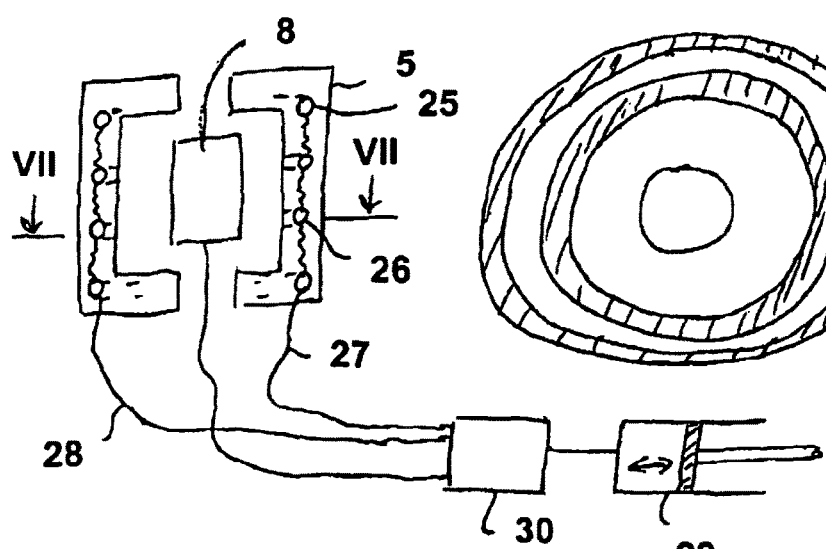
Fig. 7
Fig. 6

FUNCTIONAL ELEMENT, IN PARTICULAR FLUID PUMP, HAVING A HOUSING AND A CONVEYING ELEMENT

BACKGROUND OF THE INVENTION

The present invention resides in the field of mechanical engineering, in particular micromechanics, and can be used with functional elements which are used to convey or influence fluids.

The invention can be used particularly advantageously in medical technology, where it is made to work, in particular in invasive medicine, on body fluids, for example blood. For this purpose, micromechanical functional elements, for example pumps, are known, which have such a small construction that they can be conveyed through a blood vessel. Pumps of this type can be operated within a blood vessel itself or in a ventricle.

In order to enable a particularly efficient and effective operation, it is known to design such functional elements such that they have a compressed state in which they can be moved through a bloodstream and also an expanded or dilated state which they can adopt for example after introduction into a ventricle or another body cavity. In this expanded state, for example a pump can then have a rotor and a housing which apply sufficient pump power by means of their size and nevertheless can be introduced in the compressed state into the body and removed again therefrom.

Various techniques are known for compressing or expanding such pumps. For example, so-called shape memory materials in the form of alloys are used, one of which is known by the trade name Nitinol, the corresponding components generally adopting various geometric shapes as a function of temperature. The type of construction can be designed such that a first dimensional size is adopted in a first state of a Nitinol frame, whilst a second size is achieved in a second state at a different temperature. For example in the case of pumps, both the housings and the rotors can in principle be compressed and expanded in this way.

However pumps without rotors which transport a fluid by expulsion by means of volume changes are also known. Such a pump is known for example from DE 10 2007 012 817 A1. Use of such a toroidal pump is known there for assisting the heart, the pump being inserted in a blood vessel. The housing has a stable external shape but can be folded up. The whole pump is designed as a double chamber hollow body, a balloon which can vary within the housing effecting the volume change of a pump volume and hence suctioning in and expelling fluid. With respect to the type of housing and in addition in what manner this housing is compressible, nothing is stated in the document.

A pump is known from the public inspection document DE 4124299 A1, which has a housing which can be filled with a fluid and consequently stiffened and also a conveying element which can be pumped up therein so that alternately fluid in the housing interior can be suctioned in and expelled.

Similar pumps are known from U.S. Pat. No. 5,820,542 and U.S. Pat. No. 5,827,171.

U.S. Pat. No. 5,928,132 discloses a pump with an expandable housing which can be stiffened by means of fluid-filled cavities.

BRIEF SUMMARY OF THE INVENTION

Against the background of the state of the art, the object underlying the invention, in the case of a pump having a fluid chamber and a housing delimiting the latter and also a conveying element disposed in the fluid chamber, is to design the housing such that it can be compressed with respect to the radius and, on the other hand, can be expanded and, in the expanded state, has as high stability as possible.

The object is achieved by the features of the invention according to patent claim 1.

In the case of a pump of the initially mentioned type, the housing, with respect to the shape and/or size thereof, can be changed between at least a first, expanded state and a second, compressed state, as a result of the fact that it has at least one stabilisation chamber which can be supplied with a fluid pressure and is different from the fluid chamber, the first state of the housing being assigned to a first fluid pressure in the stabilisation chamber and the second state of the housing to a second fluid pressure.

The different filling or pressure supply to the stabilisation chambers effects different material stresses in the wall/the elastic walls of the housing. For example, the stabilisation chamber or a plurality of stabilisation chambers can be recessed on the housing walls, and this will typically lead to the fact that, at low pressure in the stabilisation chambers, the housing contracts elastically and relaxes, the housing walls become moveable and the housing diameter is reduced both with respect to the outer diameter and with respect to the inner diameter. For this purpose, at least the inner and/or the outer wall of the housing which directly surrounds the conveying element and, for its part, is possibly surrounded by stabilisation chambers or one stabilisation chamber has an elastic configuration. In the case of increased pressure, the stabilisation chambers become taut and hence the walls are for the moment widened and stiffened so that the housing expands. The states can however also be chosen such that the walls of the housing have pre-tensions which lead to the fact that, in the case of a high pressure application to the stabilisation chamber(s), compression of the housing is effected, whilst, at low pressure in the stabilisation chambers, expansion of the housing is effected due to the inherent stress of the housing walls.

It can thereby be advantageously provided that, in the second state, the diameter of the housing is reduced by the inherent elasticity to such an extent that the interaction element in its expanded state is compressed radially.

Hence, the elastic compression effect of the housing facilitates the compression of the interaction element, for example a fluid conveying element. This can have for example the form of a pump rotor.

The cavity or cavities can be provided as recesses in a solid housing wall or as intermediate space/spaces between two spaced layers of the housing wall—i.e. between an inner wall and an outer wall. Inner wall and outer wall can have an equally elastic configuration or differently elastic configuration. The outer wall can thereby have a more flexible configuration than the inner wall or the inner wall have a more flexible configuration that the outer wall.

The elasticity of the housing wall in total is advantageous such that the housing contracts elastically and without folds from the expanded state with a first inner diameter at least to half, in particular to a third, of the first diameter, when the inner pressure and also the pressure in the stiffening chambers is reduced. During compression, the housing hence makes a decisive contribution to the compression of the conveying element, in particular of the rotor.

The housing wall can be designed for example as an open-pore foam, the pores on the inner and outer side of the wall being closed, e.g. by welding or be a separate coating. If the expansion of the cavities is intended to take place by a material transport by diffusion or the like, then the open-pore foam can also be covered by a semipermeable membrane.

The structure of the cavities can also be such that a first group of cavities is open towards one of the walls of the housing, e.g. in the form of access channels or as open-pore foam, and such that one or more cavities of a second group are embedded in the first group, respectively one semipermeable membrane being provided between the first and the second chambers. For example, the semipermeable membrane can surround respectively one or more cavities of the first group or of the second group.

As partially permeable membrane for delimiting cavities, there can be used, according to the used filling materials for the cavities and the materials which are intended to be allowed through or held back, membranes of microfiltration (0.5-0.1 μm particle size), ultrafiltration (0.1-0.01 μm particle size) and nanofiltration (1-10 nm). Independently of the particle size, basically biological or synthetic membrane materials can be used (as biological materials, for example Cuprophan, Hemophan or cellulose triacetate, as synthetic membrane for example Teflon or Goretex).

Synthetic materials in general have a higher water permeability and are themselves often hydrophobic. There can be used as synthetic materials, polysylphone, polyamide, polyacrylonitrile and also copolymers thereof and also polymethylmethacrylates, polytetrafluoroethylene and derivatives thereof.

High-flux membranes are advantageously used, which allow through molecules up to a molecular weight of 50,000 Dalton and which ensure rapid material transport.

Advantageously, the material is chosen such that it retains germs/bacteria/microorganisms preventing contamination or infection.

Either a gas or a liquid, in particular a biocompatible liquid such as salt solution, can thereby be chosen as fluid for filling cavities/stiffening chambers/stabilisation chambers. Advantageously, the housing can have the shape of a hollow cylinder, a toroid or a hollow spheroid at least in portions. Such a shape basically leads to good usability of the housing in a body since these shapes can basically be moved easily through a naturally occurring body vessel. A rotational-symmetrical shape is possible in particular if the housing is used for a fluid pump. The housing is normally sealed at the ends, either by flat end-sides or by sealing surfaces which are conical or rotational-symmetrical in another way and have corresponding inflow/outflow openings.

The stabilisation chamber can be provided particularly efficiently in the form of a cavity which is strand-shaped in the first housing state. In this case, the stabilisation chamber forms a stabilisation web as it were in the housing wall in the case of high pressure application. Hence, a relatively small quantity of fluid is required in order to fill the stabilisation chamber(s) and to stabilise the house. Advantageously, a plurality, in particular three or more stabilisation chambers, can be provided in the form of strand-shaped cavities. These can be distributed symmetrically in the housing.

It can also be provided advantageously that at least one strand-shaped cavity (viewed in the expanded state of the housing) has a circumferential configuration in the circumferential direction of the hollow cylinder, toroid or hollow spheroid. In this case, a particularly efficient stabilisation structure for the housing is produced, which counteracts in particular a compression of the housing during pressure application to the stabilisation chamber. This is particularly advantageous when the functional element is designed as a fluid pump and a suction pressure is produced within the housing at least at times in order to suction in body fluid, in particular blood. At this moment, the housing is sensitive to the tendency to collapse and must in particular be stabilised relative to this compression. Also a toroidal or hollow cylinder-shaped body can be provided as stabilisation chamber.

Alternatively or additionally to a strand-shaped cavity as stabilisation chamber, which extends in circumferential direction, one or more strand-shaped cavities can extend parallel to the longitudinal axis of the hollow cylinder, toroid or hollow spheroid in the wall thereof. In this way, a stabilisation grating can be formed, which, at a low total volume of the stabilisation chambers, allows good stabilisation and a good, i.e. a high ratio, between the radius of the housing in the expanded state and the radius in the compressed state.

It can also advantageously be provided that the stabilisation chamber essentially fills the space of the housing wall. As a result, the structure of the housing is simplified and this can be filled or also emptied again rapidly and without complication by pressure application. The housing can then have for example the shape of a hollow-walled balloon.

In many case, it can be provided for stabilisation that the corresponding cavities are penetrated by webs of the housing material. In this way, stabilisation of the housing even relative to a relative movement of inner and outer walls is achieved.

On its housing, the fluid pump has an inflow opening and an outflow opening which can be provided respectively with a valve, in particular a one-way valve. It can be ensured in this way that the function is optimised during use as a pulsating pump with a suction phase and an expulsion phase. Body fluid is then suctioned in through the inflow opening, whilst this is conducted out through the outflow opening in the expulsion phase.

Basically, such a housing can also be provided with a conveying element which is designed as rotor with at least one blade for the fluid. It can thereby be provided that the conveying element is radially compressible by folding in, folding up or collapsing the conveying blades.

The blade/blades can thereby be flexible elastically radially towards the rotor axis.

However, the rotor can also consist at least partially of a volume-compressible material, in particular a foam.

Additionally or alternatively to the housing, the rotor can likewise have compressible cavities.

The rotor can thereby also be configured without a hub, the blade being stabilised in a self-supporting manner as conveying surface and transmitting the torque.

In connection with the present invention, the advantage of a compressible rotor resides in the fact that the latter is at least partially compressed already by the contraction of the housing so that no high additional forces require to be applied when the fluid pump must be moved through a blood vessel in a body.

A further advantage of the elastic contraction of the housing resides in the fact that the forces act regularly radially inwards on the rotor. If the housing collapses when it is merely relaxed, then the effect on the rotor is not reproducible.

Advantageously, it can also be provided that the conveying element is designed as a fluid-Tillable hollow body/balloon which can hence be changed with respect to its volume. Hence, it is achieved that expulsion in the interior/fluid chamber of the housing takes place with pressure application to the hollow body so that the fluid situated there is expelled. If the pressure application to the hollow body is reduced, then the latter is compressed by the elasticity of its walls and frees additional volume in the housing so that fluid from outside is suctioned into the fluid chamber of the housing.

Hence a pulsating pump is produced for conveying the fluid. Advantageously, the conveying element in the filled form can essentially fill the fluid chamber of the housing. Hence, the stroke of the pump is optimised when fluid is suctioned in and expelled.

Advantageously, the conveying element can be filled with the same fluid as the stabilisation chamber(s). Since both the stabilisation chamber(s) and the conveying element must be supplied with pressure after introduction of the functional element into the body, great simplification is produced if the same fluid can thereby be used. Normally, a biocompatible fluid, for example a salt solution, is used. However, also the use of a gas, for example a bioinert gas such as helium, is conceivable.

Handling is further simplified by the conveying element and the stabilisation chambers of the housing being able to be connected to the same fluid pressure source.

The object of the invention, to produce a fluid pump having a compressible housing, is also achieved by the following functional element. Involved hereby is a fluid pump having a housing delimiting a fluid chamber and having a conveying element for the fluid disposed in the fluid chamber, both the housing and the conveying element, with respect to the shape and/or size thereof, being able to be changed between at least a first, expanded state and a second, compressed state, the average change in density of the housing material between the first and the second state being at least 10%.

There is hereby meant the average change in density of the housing material at constant temperature, for example 36° C. The local change in density of the housing can vary greatly, what is crucial is the average change in density of the housing material, this housing material not requiring at all to be homogeneous, but rather for example metallic parts can also be a component here which would then have a correspondingly smaller change in density.

Preferably, reversibly or even irreversibly deformable materials should be provided here, which, because of an osmotic mode of operation in the decompressed state, have a greater volume/smaller density, or foams which have a smaller density in the decompressed state. These foams can be open-pore or closed-pore.

The housing is preferably distinguished by a material mixture or a material which can be converted by compression from a first, lower density or from a first, lower specific weight to a second, higher density or a higher specific weight. The cavities can thereby be closed and filled with a gas, such as for example air or nitrogen, or a noble gas or another bioinert gas which can be compressed easily in volume by pressure.

Such closed cavities tend to expand again in the absence of an external pressure force due to the gas elasticity so that the housing, as soon as it is brought to the place of use, can unfold again automatically. At least the unfolding movement is assisted however by the gas elasticity.

In addition, also gas lines to the housing can however be provided, which gas lines end in one or more cavities and actively allow the cavities to be pumped up. The gas for the compression can possibly also be suctioned out via the same lines.

Likewise, the operation can take place with a liquid if this is introduced into the cavities. If a liquid is situated in the cavities, then this is normally very much less compressible but, due to suitable choice of the viscosity in cooperation with the remaining constructional parts of the housing, it can enable high moveability and hence compressibility nevertheless support a certain housing stability during operation due to the incompressibility after unfolding of the housing.

The cavities can also have an open design, hence high compressibility likewise being provided. The material which delimits the cavities must then have a correspondingly elastic configuration. This can be provided for example in the case of an open-pore foam.

The invention can also be implemented advantageously by the cavity/cavities being at least partially delimited by a partially permeable membrane.

In this case, a cavity can be filled with a liquid which, together with the membrane used and as a function of the liquid in which the pump can be inserted, in particular human blood, allows diffusion into the cavity as a result of osmosis, which leads to an increase in pressure and to pumping-up of the housing.

Likewise, also materials can be used which, after coming in contact with the liquid to be conveyed, lead to swelling processes as a result of absorption of the liquid and hence assist decompression of the housing via an increase in volume.

In the case of the osmosis process, filling the cavities with a salt or a salt solution, the salt concentration of which is higher than that of the liquids to be conveyed, is possible. For this purpose, also semipermeable membranes which surround fluid-filled stabilisation chambers at least partially and which can be designed as biological or synthetic membranes, for example cellulose-based, are then provided.

Advantageously, it can also be provided that at least the predominant part of the cavities is surrounded by solid material of the housing and connected via openings to the outside and/or to each other. In this case, during compression, a fluid transport can take place via the cavities and possibly also out of the housing so that the corresponding cavities can be easily compressed entirely.

The housing can consist for example partially of a porous material, such as foam, in particular polyurethane. Such a foam can be open- or closed-pore. In the case of an open-pore foam, the elasticity is based on the supporting material which surrounds the pores and moves after compression by itself back into its original form, the gas or fluid being able to flow back into the pores. Due to the limited flow cross-sections of the connections of the cavities/pores to each other, a time constant in the compression/decompression can be chosen within specific limits. This can ensure, during operation of the pump, that sudden deformations of the housing due to irregular mechanical loading are counteracted.

It can be provided to produce such a housing by injection of a foam into a pre-manufactured mould.

BRIEF DESCRIPTION OF THE DRAWINGS

The invention is shown in a drawing and subsequently described with reference to an embodiment in the following.

There are thereby shown

DETAILED DESCRIPTION OF THE INVENTION

Figures 1, 2, 3:
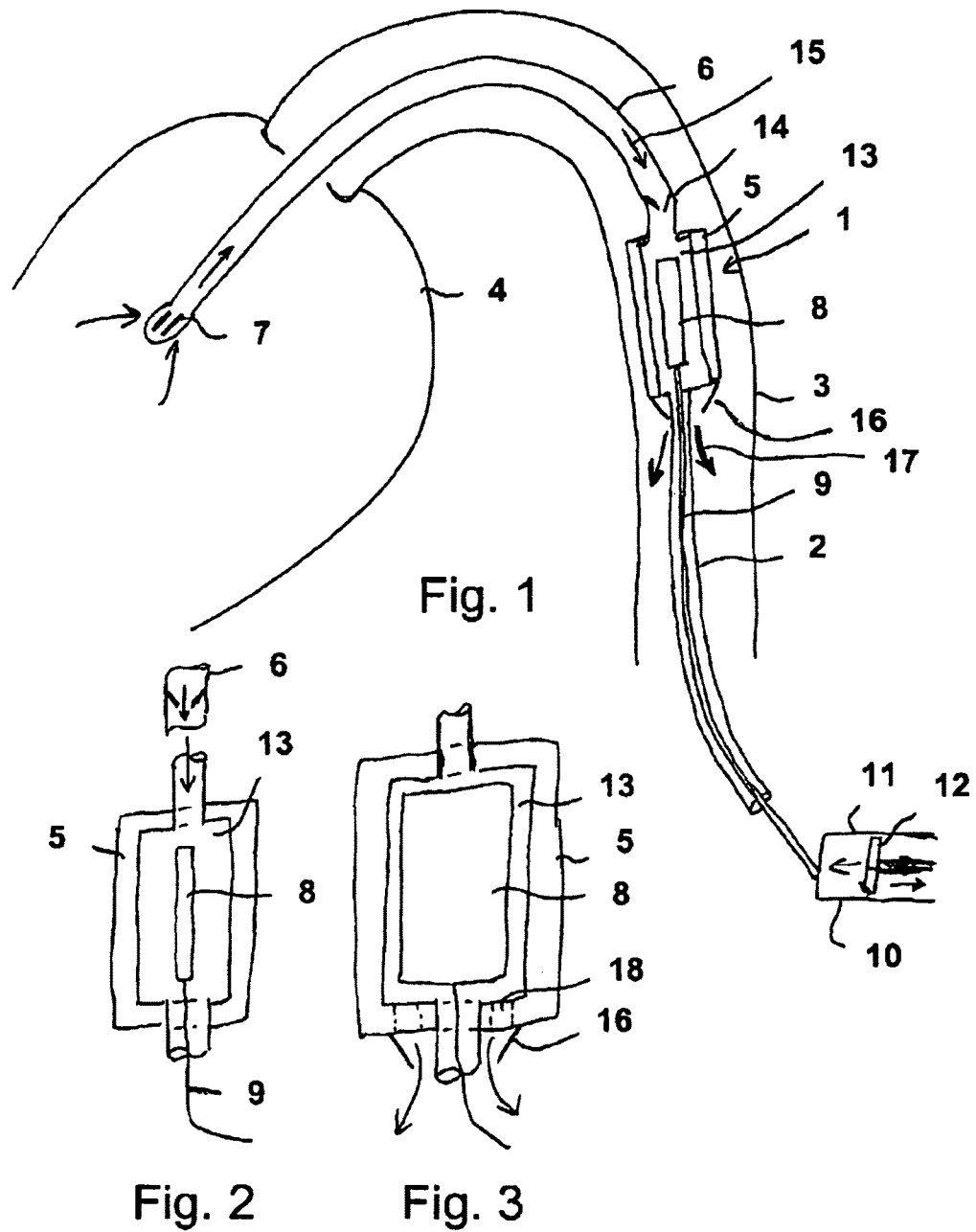
FIG. 1 an overview of the use of a fluid pump according to the invention in a blood vessel, FIG. 2 a longitudinal section through a fluid pump with a compressed conveying element, FIG. 3 a longitudinal section as in FIG. 2 with an expanded conveying element, FIG. 4 a longitudinal section through a housing with stabilisation chambers, FIG. 5 a cross-section through the construction according to FIG. 4, FIG. 6 a longitudinal section through a housing having a further configuration of stabilisation chambers, FIG. 7 a cross-section as indicated in FIG. 6, FIG. 8 a longitudinal section through a hollow balloon-like housing in spheroid form, FIG. 9 a longitudinal section through the functional element in total in compressed form, FIG. 10 a fluid pump in longitudinal section having a pump rotor, FIG. 11 in a side view, a hub-free rotor and FIG. 12 a detailed view of a pore structure.

FIG. 1 shows the functional element 1 in the form of a fluid pump in a section, inserted in the human body. The fluid pump is introduced by means of a hollow catheter 2 into a blood vessel 3 which leads to a ventricle 4. The housing 5 of the fluid pump is connected to the interior of the ventricle 4 via a suction hose 6 which extends through the blood vessel 3 and the suction hose there has one or more suction openings 7. The suction hose 6 is rounded off at its end in the vicinity of the suction openings 7 in order to avoid injuries to the interior of the heart.

Within the housing 5 of the fluid pump, a conveying element 8 in the form of a balloon is situated, in the present case essentially in cylindrical form, which balloon is connected via a pressure line 9 to a pressure source 10 outside the body. The pressure line 9 extends through the hollow catheter 2 and both are guided out of the blood vessel 3 to the outside of the body in a lock, not represented.

The pressure source 10 is shown only schematically in the form of a cylinder 11 and a piston 12 which is moveable therein, the piston producing, during a pulsating movement, a likewise pulsating pressure which leads to an alternating expansion and compression of the conveying element 8.

As a result, the conveying element 8 in the interior of the housing 5 takes up more or less space alternately so that, as a countermove, more or less space remains available for the fluid to be conveyed in the fluid chamber 13 of the housing 5. The fluid is hence expelled and suctioned in by the conveying element 8 in a pulsating manner.

By using valve flaps, the fluid flow is directed in the desired form. In the illustrated example, valve flaps 14 are provided in the suction line 6 and allow the fluid to flow in in the direction of the arrow 15. The valve flaps could be provided equally well in the corresponding opening of the housing 5. Thereby involved is a return- or one-way valve which allows the fluid to flow in the direction of the arrow 15 but not to flow out in the opposite direction. This leads to the fact that, during compression of the conveying element 8, fluid, i.e. in particular blood, can be suctioned via this path, but that this cannot flow out again there during expansion of the conveying element.

Outflow flaps 16 which can be disposed for example directly on the housing 5 and which likewise allow the fluid to flow out in only one direction, namely in the direction of the arrow 17, are provided for the outflow.

With cooperation of the valve flaps 14, 16, it is ensured that the fluid is conveyed from the fluid pump only in the direction of the arrows 15, 17.

The throughput of the fluid pump is determined, apart from the residual power of the patient's heart as long as this is still functioning, by the pulsating frequency of the conveying element 8, on the one hand, and by the volume expelled respectively by the conveying element or by the free volume remaining in the fluid chamber 13. The conveyance is maximised when the conveying element can expand to completely fill the fluid chamber 13 and thereafter collapses so far that its interior is completely emptied. The conveying element can consist for this purpose of a highly elastic material which, after lowering the pressure in the pressure line 9, ensures compression of the conveying element. This leads to a pressure drop in the fluid chamber 13, as a result of which further fluid is suctioned subsequently.

However, it is a prerequisite for functioning of this mechanism that the housing 5 remains stable and does not collapse even when producing a low pressure in its interior. This requirement is connected, according to the invention, to the further requirement that the housing must be compressible for introduction and removal into and out of a body.

The invention provides for this purpose that the housing is provided with at least one stabilisation chamber which stiffens the housing as a result of pressure application.

In an extreme case, the entire housing can be configured thereby as a double-walled balloon, the space between the balloon walls being typically at a higher pressure, in the expanded state, than the space of the blood vessel surrounding the housing. It can also be provided that this pressure is higher than the pressure prevailing at most in the conveying element and in the fluid chamber.

FIG. 2 shows schematically the state of a fluid pump having a hollow cylindrical housing 5 and a compressed conveying element 8 in the suction phase. The fluid chamber 13 is essentially filled with the fluid flowing through the suction line 6.

The conveying element 8 has an essentially cylindrical form and consists for example of rubber or polyurethane or an elastomer with similar properties, the surface of the conveying element being able to be coated with a material which, on the one hand, prevents infections and, on the other hand, avoids accumulation of blood on the surface. The same coating can be provided in the interior of the housing 5 on the walls thereof.

The conveying element 8 is connected to a pressure source via a pressure line 9 which is essentially designed not to be expandable.

FIG. 3 shows the configuration of FIG. 2 in an expanded state of the conveying element 8 in which the free residual space of the fluid chamber 13 is minimised and the fluid/the blood can flow out of openings 18 of the housing 5 through valve flaps 16.

It should be noted than the housing 5 with respect to its outer diameter can be configured such that it does not completely fill the clear opening of the blood vessel 3 so that, when inserted into a body, blood can be conveyed through the vessel 3 by the inherent function of the heart, in addition to the fluid pump. However, it is also conceivable that the diameter of the blood vessel is completely filled by a suitably chosen diameter also for specific purposes.

In FIG. 4, the strengthening of the housing 5 by stabilisation chambers is dealt with in more detail. In this embodiment, a plurality of strand-shaped stabilisation chambers 19, 20 is aligned parallel to the longitudinal axis 21 of the housing 5 and disposed in the housing wall.

FIG. 5 shows a cross-section with seven such stabilisation chambers. The individual stabilisation chambers are separated from each other in this case and connected individually to a fluid pressure source via pressure lines 22, 23, 24. The stabilisation chambers can be supplied with pressure in order to stiffen the housing 5. In order to introduce or remove the housing 5, they are emptied so that the housing 5 can collapse on itself.

The stabilisation chambers can also be connected amongst each other via a pressure line in order to ensure that the same pressure respectively prevails in them and in order to simplify filling and emptying.

FIG. 6 shows another arrangement of the stabilisation chambers in the form of annular strands which are disposed respectively coaxially to each other and to the housing 5. The stabilisation chambers are designated with 25, 26. In the embodiment, four of these stabilisation chambers are provided equidistant from each other in the housing wall. They are connected to a pressure source 29 by means of pressure lines 27, 28.

Such annular or even possible, helical stabilisation chambers offer particularly good stiffening of the housing and, during pressure application, a corresponding resistance to the pulsating low pressure in the housing interior.

In the embodiment, the stabilisation chambers and the conveying element 8 are connected to the same pressure source 29 via a multi-way control valve 30. As a result, the pressure source 29 can be used both for filling the stabilisation chambers and for the pulsating pumping of the conveying element 8. FIG. 7 shows a cross-section through the housing represented in FIG. 6 in longitudinal section with a toroidal stabilisation chamber 26.

Figure 8:
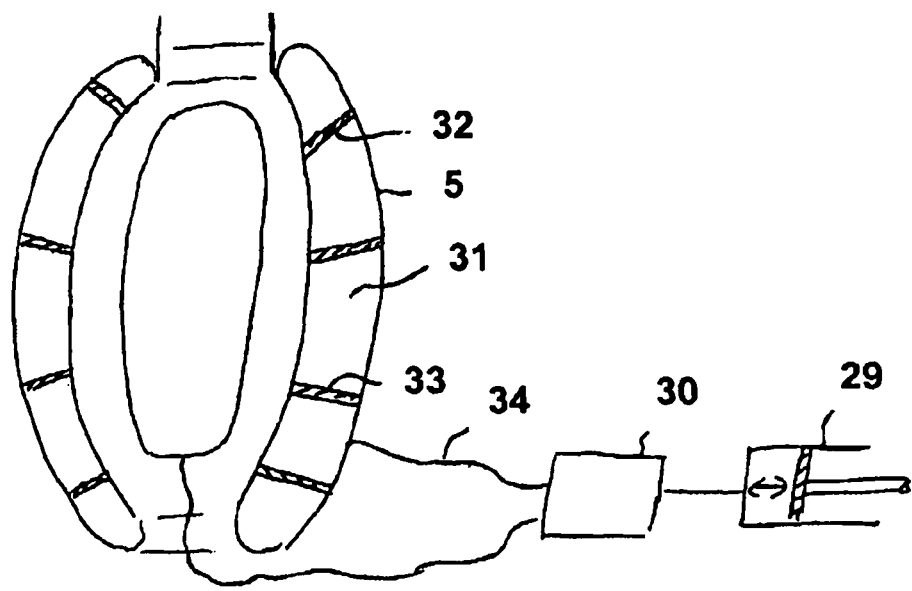

In FIG. 8, another concept of the housing within the scope of the invention is represented, in which the housing wall is double-walled, the two outer walls (balloon walls) have a very thin design and the housing is hence constructed in the manner of a balloon. The housing forms a double-walled balloon having a large cavity 31 which can however be subdivided into a plurality of partial chambers. Either thin intermediate walls are provided for this purpose or, if no complete subdivision is desired, also only individual reinforcing struts in the form of webs 32, 33 can be provided. These ensure that inner wall and outer wall of the balloon cannot perform shear movements relative to each other so that the housing 5 in total is stabilised. The interior 31 is connected to the pressure source 29 by means of a pressure line 34. The housing 5 has in total the contour of a spheroid.

The stabilisation struts 32, 33 can typically consist of the same material as the balloon walls of the housing 5 and be produced in one piece with the latter. The struts can thereby surround the housing 5 annularly or be configured as axis-parallel webs. However, also any orientation, for example even a grating-shaped structure, is conceivable.

Likewise, also in the above-described embodiments not only is the concretely described orientation of the strand-shaped stabilisations chambers conceivable but also a grating-shaped or network-shaped structure there which penetrates a solid housing wall.

Figure 9:
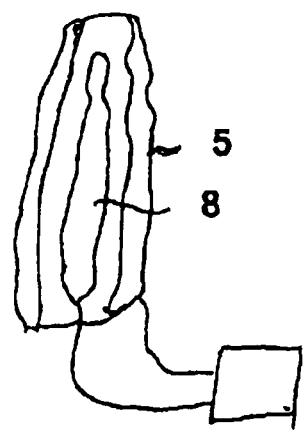

In FIG. 9, finally the collapsed shape of the housing represented in FIG. 8 is shown, the spheroid being collapsed. The conveying element 8 must likewise be compressed of course for introducing/removing the fluid pump into a blood vessel.

For removal of the fluid pump from the vessel, it can provided that firstly the housing 5 is collapsed by reducing the pressure in the stabilisation chambers and only thereafter is the conveying element 8 emptied. As a result, an oblong shape is produced when the housing 5 is folded up and the latter is predominantly prevented from collapsing in the longitudinal direction and hence adopting a higher cross-section. The elastic contraction of the housing can thus also assist compression of the conveying element.

By means of the invention, a functional element is formed which is compressible to a high degree and nevertheless has the necessary stability in operation to resist both low and high pressures in a dimensionally stable manner during pulsating pumping.

Figure 10:
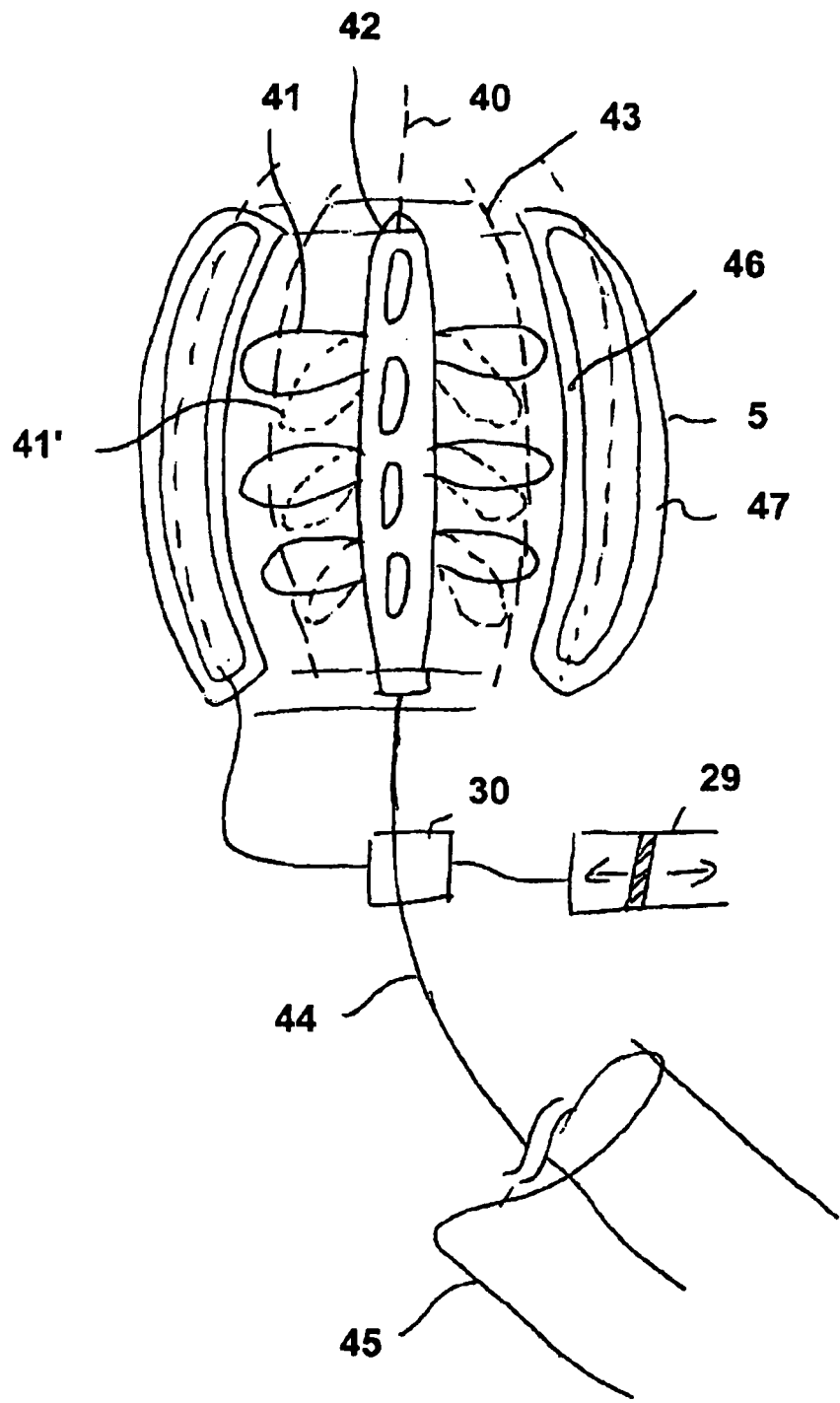

In FIG. 10, a housing 5 similar to that represented in FIG. 9 is shown, which however surrounds a pump rotor here, which rotates about its longitudinal axis 40 and thereby conveys a fluid axially. The blades 41 can thereby be secured individually to branch off on a shaft 42 or also a helically circumferential blade can be provided. The rotor is radially compressible and can be manufactured for example from a framework comprising a memory alloy, for example Nitinol, or from another elastic material. The rotor can have open or closed cavities in the blades and/or the hub which are elastically compressible. In FIG. 10, the inner wall of the housing is designated with 46, the outer wall with 47. At least the inner wall can be widened and contracted elastically. A contracted state of the housing 5 is represented in broken lines and the inner wall is designated with 43. This presses the blades 41', in the represented state, into a radially bent-in state so that the entire rotor is already reduced in size by some distance radially.

Figure 11:
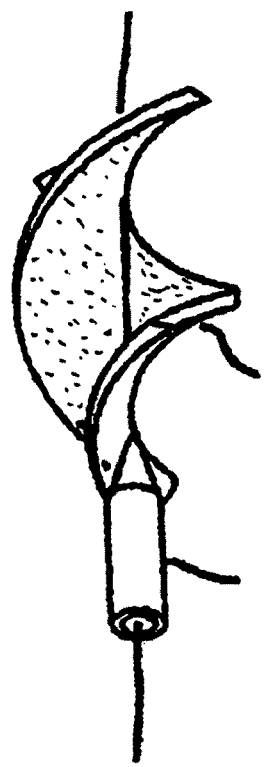

In FIG. 11, a hub-free rotor which can also be used is represented and consists of a helically bent flat plate. This can consist for example of an easily deformable or compressible material, such as for example a sheet metal grating covered with foil or a foam, the rotor which is represented as open-pore or closed-pore is hub-free and self-supporting, i.e. the blade itself transmits the torque and is only mounted outside rotatably and connected to a driveshaft 44 (FIG. 10) which extends through a hollow catheter 45.

Figure 12:
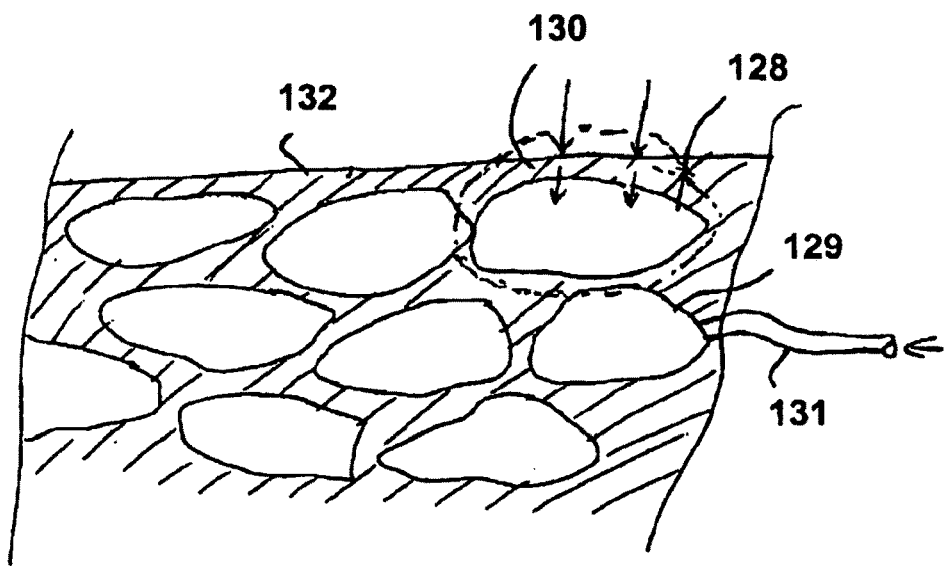

FIG. 12 shows, in greatly enlarged, microscopic representation, a housing material in the form of a foam 132 having closed pores 128, 129, the material of the walls between the pores being configured, in a variant (cavity 128), as a semipermeable membrane.

Such a membrane allows the diffusion of specific liquids, which can be used for example for an osmotic effect. If the cavities/pores 128 are filled for example with a liquid in which a salt in a highly concentrated form is dissolved and if the foam is brought into a liquid which has a lower solution concentration, then the combination tends to bring the concentrations of both liquids to approximate to each other such that the solvent diffuses from outside into the interior of the cavity 128 through the membrane 130. As a result, an increased osmotic pressure is produced and can be used to pump up the cavity 128 into the shape represented in broken lines. As a result, an expansion and stiffening of the foam can be achieved.

This effect can also be used specifically for larger cavities in the housing. Alternatively, also swelling processes can be used to expand the rotor.

In connection with the cavity 129, a hose 131 is represented and symbolises that corresponding cavities can also be filled with a fluid via individual or collective supply lines or that such a fluid can be suctioned out of them in order to control corresponding decompression/compression processes.

The invention claimed is:

1. A fluid pump comprising:
   a housing delimiting a fluid chamber, the housing having a proximal end connected to a catheter and a distal end, the housing being changeable between at least a first, expanded state and a second, compressed state, the housing having: an inner wall, an outer wall, at least one stabilization chamber, different from the fluid chamber, disposed between the inner wall and the outer wall, wherein the stabilization chamber can be supplied with a fluid pressure, the first state of the housing corresponding to a first fluid pressure in the stabilization chamber and the second state of the housing corresponding to a second fluid pressure in the stabilization chamber, and at least one of the inner and outer wall of the housing being elastic and configured to contract elastically into the second state during the transition from the first into the second state, wherein the housing is configured to be positioned within a blood vessel outside of the aortic valve, and wherein an outer diameter of the housing is smaller than an inner diameter of the blood vessel when the housing is in the first state;

a radially compressible rotor disposed in the fluid chamber and having at least one blade; and an elongate cannula configured to be positioned across an aortic valve, the elongate cannula also being connected to the distal end of the housing and in communication with the fluid chamber;

wherein in the second state, a diameter of the housing is reduced by the elasticity in its expanded state to such an extent that the rotor is compressed radially by the inner wall.

2. The fluid pump according to claim 1, wherein the first fluid pressure of the first state in the at least one stabilization chamber is higher than the second fluid pressure of the second state.

3. The fluid pump according to claim 2, wherein the housing has the shape of a hollow cylinder, a toroid or a hollow spheroid at least in portions.

4. The fluid pump according to claim 3, wherein the stabilization chamber is in the form of elongated cavities in the expanded housing state.

5. The fluid pump according to claim 4, wherein at least three stabilization chambers in the form of elongated cavities are provided in the first expanded state.

6. The fluid pump according to claim 4, wherein the elongated cavities have an annularly or helically circumferential configuration in the circumferential direction of the hollow cylinder, toroid or hollow spheroid.

7. The fluid pump according to claim 6, wherein at least one stabilization chamber extends parallel to the longitudinal axis of the hollow cylinder, toroid or hollow spheroid in the wall thereof.

8. The fluid pump according to claim 3, wherein the at least one stabilization chamber essentially fills the space of the housing wall.

9. The fluid pump according to claim 8, wherein the at least one stabilization chamber is penetrated at least partially by respectively at least one web.

10. The fluid pump according to claim 9, wherein the housing has the shape of a hollow-walled balloon.

11. The fluid pump according to claim 10, wherein the housing has an inflow opening and an outflow opening which are provided respectively with a valve.

12. The fluid pump according to claim 1, wherein the at least one blade is flexible elastically radially towards the rotor axis.

13. The fluid pump according to claim 12, wherein the rotor consists at least partially of a volume-compressible material.

14. The fluid pump according to claim 13, wherein the rotor has compressible cavities.

15. The fluid pump according to claim 14, wherein the rotor is designed to be hub-free.

16. The fluid pump according to claim 15, wherein the rotor is designed at least in part as a fluid-fillable balloon.

17. The fluid pump according to claim 10, wherein the rotor in the filled form essentially fills the fluid chamber of the housing.

18. The fluid pump according to claim 1, wherein the rotor is filled with the same fluid as the at least one stabilization chamber.

19. The fluid pump according to claim 12, wherein the rotor and the at least one stabilization chamber of the housing can be connected to the same fluid pressure source.

20. The fluid pump according to claim 4, wherein the stabilization chamber is within a housing wall.

21. The fluid pump according to claim 11, wherein the valve is a one-way valve.

22. The fluid pump according to claim 13, wherein the material is foam.

23. The fluid pump of claim 1, wherein the elongate cannula extends from a blood vessel into a ventricle of a human body.

24. The fluid pump of claim 1, wherein the catheter is configured to provide the first fluid pressure to the stabilization chamber.

25. The fluid pump of claim 1, wherein the stabilization chamber comprises an inflatable region, the inflatable region having a distal end and a proximal end, and wherein a distal end of the rotor is positioned proximal to the distal end of the inflatable region when the housing is in the first state.

26. The fluid pump of claim 1, wherein the at least one blade is helical.

27. The fluid pump of claim 1, wherein the stabilization chamber includes at least one reinforcing strut extending between the inner wall and the outer wall, the reinforcing strut configured to prevent shear movements between the inner wall and the outer wall.

* * * * *

UNITED STATES PATENT AND TRADEMARK OFFICE
CERTIFICATE OF CORRECTION

PATENT NO. : 10,107,299 B2
APPLICATION NO. : 13/261216
DATED : October 23, 2018
INVENTOR(S) : Mario Scheckel Page 1 of 1

It is certified that error appears in the above-identified patent and that said Letters Patent is hereby corrected as shown below:

In the Specification

Column 4, Line 62, delete "fluid-Tillable" and replace with --fluid-fillable--

Signed and Sealed this
Fourth Day of December, 2018

Andrei Iancu
*Director of the United States Patent and Trademark Office*